(12) United States Patent
Gilson et al.

(10) Patent No.: US 10,500,065 B2
(45) Date of Patent: Dec. 10, 2019

(54) ORTHOPAEDIC SURGICAL INSTRUMENT EXTRACTION SYSTEM AND METHOD

(71) Applicant: DEPUY IRELAND UNLIMITED COMPANY, Ringaskiddy, Co Cork (IE)

(72) Inventors: Lindsay L. Gilson, Winona Lake, IN (US); Jeffrey M. Walcutt, Fort Wayne, IN (US); Thomas E. Wogoman, Warsaw, IN (US); Daren L. Deffenbaugh, Winona Lake, IN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 240 days.

(21) Appl. No.: 15/704,087

(22) Filed: Sep. 14, 2017

(65) Prior Publication Data

US 2019/0076271 A1 Mar. 14, 2019

(51) Int. Cl.
*A61B 17/58* (2006.01)
*A61B 17/60* (2006.01)
*A61F 2/00* (2006.01)
*A61F 2/46* (2006.01)
*A61F 2/38* (2006.01)
*A61F 2/36* (2006.01)
*A61F 2/30* (2006.01)

(52) U.S. Cl.
CPC .......... *A61F 2/4603* (2013.01); *A61F 2/3609* (2013.01); *A61F 2/389* (2013.01); *A61F 2/3859* (2013.01); *A61F 2/4637* (2013.01); *A61F 2/4684* (2013.01); *A61F 2002/30329* (2013.01); *A61F 2002/4619* (2013.01)

(58) Field of Classification Search
CPC combination set(s) only.
See application file for complete search history.

(56) References Cited

U.S. PATENT DOCUMENTS

| 5,194,066 A | 3/1993 | Van Zile |
| 5,464,406 A | 11/1995 | Ritter |
| 6,120,509 A | 9/2000 | Wheeler |
| 6,146,385 A * | 11/2000 | Torrie ................ A61B 17/1635 606/80 |
| 2005/0125067 A1 | 6/2005 | Sweeney |

OTHER PUBLICATIONS

Extended European Search Report dated Feb. 6, 2019, 7 pages.

* cited by examiner

*Primary Examiner* — Sameh R Boles
(74) *Attorney, Agent, or Firm* — Barnes & Thornburg LLP

(57) ABSTRACT

A surgical instrument extraction system includes a first extraction tool having a first body that extends between a first end and a second end. The first extraction tool has a first plurality of threads formed on the first end and a second plurality of threads formed on the second end. A second extraction tool has a second body that extends between a first end having a first diameter and a second end having a second diameter greater than the first diameter. The second extraction tool has a first plurality of threads formed on the first end and a second plurality of threads formed on the second end The first body of the first extraction tool is sized to extend through a bore of the second extraction tool. The second body of the second extraction tool is sized to extend through a bore of the first extraction tool.

10 Claims, 15 Drawing Sheets

ORTHOPAEDIC SURGICAL INSTRUMENT EXTRACTION SYSTEM AND METHOD

TECHNICAL FIELD

The present disclosure relates generally to an orthopaedic surgical instrument system, and, more particularly, to instruments for use in extracting tibial or femoral surgical instruments from a patient's bone.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis.

SUMMARY

According to one aspect of the disclosure, a surgical instrument extraction system includes a first extraction tool having a first body that extends between a first end and a second end. The first extraction tool has a first plurality of threads formed on the first end and sized and shaped to selectively couple to a threaded end of a stem component of a femoral trial system and a stem component of a tibial trial system. The first extraction tool has a second plurality of threads formed on the second end and sized and shaped to selectively couple to a stem stabilizer of a femoral intramedullary adaptor. The first extraction tool has a first bore extending through the body between the first end and the second end. A second extraction tool has a second body that extends between a first end having a first diameter and a second end having a second diameter greater than the first diameter. The second extraction tool has a first plurality of threads formed on the first end and sized and shaped to selectively couple to an intermediate trial component of a tibial trial system. The second extraction tool has a second plurality of threads formed on the second end and sized and shaped to selectively couple to an intermediate trial component of a femoral trial system. The second extraction tool has second bore extending through the second body between the first end and the second end. The first body of the first extraction tool is sized to extend through the second bore of the second extraction tool to couple the first extraction tool to the second extraction tool to provide leverage to the second extraction tool to aid in extraction. The second body of the second extraction tool is sized to extend through the bore of the first extraction tool to couple the second extraction tool to the first extraction tool to provide leverage to the first extraction tool to aid in extraction.

In some embodiments, the first plurality of threads of the first extraction tool may be female threads that are sized and shaped to couple to a male thread of the stem component of a femoral trial system and a male thread of the stem component of a tibial trial system. In some embodiments, the second plurality of threads of the first extraction tool may be male threads that are sized and shaped to couple to a female thread of the stem stabilizer. In some embodiments, the stem component of the femoral trial system may couple to the intermediate trial component of the femoral trial system. In some embodiments, the stem component of the tibial trial system may couple to the intermediate trial component of the tibial trial system. In some embodiments, the stem component of the femoral trial system may be a femoral stem trial. In some embodiments, the stem component of the tibial trial system may be a tibial stem trial.

In some embodiments, the first plurality of threads of the second extraction tool may be male threads that are sized and shaped to couple to a female thread of the intermediate trial component of a tibial trial system. In some embodiments, the second plurality of threads of the second extraction tool may be male threads that are sized and shaped to couple to a female thread of the intermediate trial component of a femoral trial system. In some embodiments, the first plurality of threads of the second extraction tool may have a first thread diameter and the second plurality of threads of the second extraction tool may have a second thread diameter. The second thread diameter may be greater than the first thread diameter. In some embodiments, the first end of the second extraction tool may be a tapered end that tapers from the second body to the first diameter. In some embodiments, the tapered end may be sized and shaped to be received in a bore extending through a side of the stem stabilizer to remove the stem stabilizer from the femoral intramedullary adaptor. In some embodiments, the intermediate trial component of a tibial trial system may couple to a surface tibial trial of the tibial trial system. In some embodiments, the intermediate trial component of the femoral trial system may couple to a surface femoral trial of the femoral trial system. In some embodiments, the intermediate trial component of a tibial trial system may be at least one of a fixed bearing adaptor trial, a fixed bearing stem adaptor trial, a rotating platform stem adaptor trial, or a tibial offset adaptor trial. In some embodiments, the intermediate trial component of the femoral trial system may be at least one of a boss adaptor trial or a femoral offset adaptor trial.

According to another aspect of the disclosure, a femoral trial system has a surface femoral trial, an intermediate trial component, a stem component. A tibial trial system has a surface tibial trial, an intermediate trial component, and a stem component. A femoral intramedullary adaptor has a stem stabilizer. A first extraction tool has a body that extends between a first end and a second end. The first extraction tool has a first plurality of threads formed on the first end and sized and shaped to selectively couple to a threaded end of the stem component of a femoral trial system and the stem component of a tibial trial system. The first extraction tool has a second plurality of threads formed on the second end and sized and shaped to selectively couple to the stem stabilizer of the femoral intramedullary adaptor. The first extraction tool has a first bore extending through the body between the first end and the second end. A second extraction tool has a second body that extends between a first end having a first diameter and a second end having a second diameter greater than the first diameter. The second extraction tool has a first plurality of threads formed on the first end and sized and shaped to selectively couple to the intermediate trial component of a tibial trial system. The second extraction tool has a second plurality of threads formed on the second end and sized and shaped to selectively couple to the intermediate trial component of a femoral trial system. The second extraction tool has a second bore extending through the second body between the first end and the second end. The first body of the first extraction tool is sized to extend through the second bore of the second extraction tool to couple the first extraction tool to the second extraction tool to provide leverage to the second extraction tool to aid in extraction. The second body of the second extraction tool is sized to extend through the bore of the first extraction tool to couple the second extraction tool to the first extraction tool to provide leverage to the first extraction tool to aid in extraction.

In some embodiments, the first plurality of threads of the first extraction tool may be female threads that are sized and shaped to couple to a male thread of the stem component of a femoral trial system and a male thread of the stem component of a tibial trial system. In some embodiments, the second plurality of threads of the first extraction tool may be male threads that are sized and shaped to couple to a female thread of the stem stabilizer. In some embodiments, the stem component of the femoral trial system may couple to the intermediate trial component of the femoral trial system. In some embodiments, the stem component of the tibial trial system may couple to the intermediate trial component of the tibial trial system. In some embodiments, the stem component of the femoral trial system may be a femoral stem trial. In some embodiments, the stem component of the tibial trial system may be a tibial stem trial.

In some embodiments, the first plurality of threads of the second extraction tool may be male threads that are sized and shaped to couple to a female thread of the intermediate trial component of the tibial trial system. In some embodiments, the second plurality of threads of the second extraction tool may be male threads that are sized and shaped to couple to a female thread of the intermediate trial component of the femoral trial system. In some embodiments, the first plurality of threads of the second extraction tool may have a first thread diameter and the second plurality of threads of the second extraction tool may have a second thread diameter. The second thread diameter may be greater than the first thread diameter. In some embodiments, the first end of the second extraction tool may be a tapered end that tapers from the second body to the first diameter. In some embodiments, the tapered end may be sized and shaped to be received in a bore extending through a side of the stem stabilizer to remove the stem stabilizer from the femoral intramedullary adaptor. In some embodiments, the intermediate trial component of a tibial trial system may couple to a surface tibial trial of the tibial trial system. In some embodiments, the intermediate trial component of the femoral trial system may couple to a surface femoral trial of the femoral trial system. In some embodiments, the intermediate trial component of a tibial trial system may be at least one of a fixed bearing adaptor trial, a fixed bearing stem adaptor trial, a rotating platform stem adaptor trial, or a tibial offset adaptor trial. In some embodiments, the intermediate trial component of the femoral trial system may be at least one of a boss adaptor trial or a femoral offset adaptor trial.

BRIEF DESCRIPTION OF THE DRAWINGS

The detailed description particularly refers to the following figures, in which.

DETAILED DESCRIPTION OF THE DRAWINGS

Figure 1:
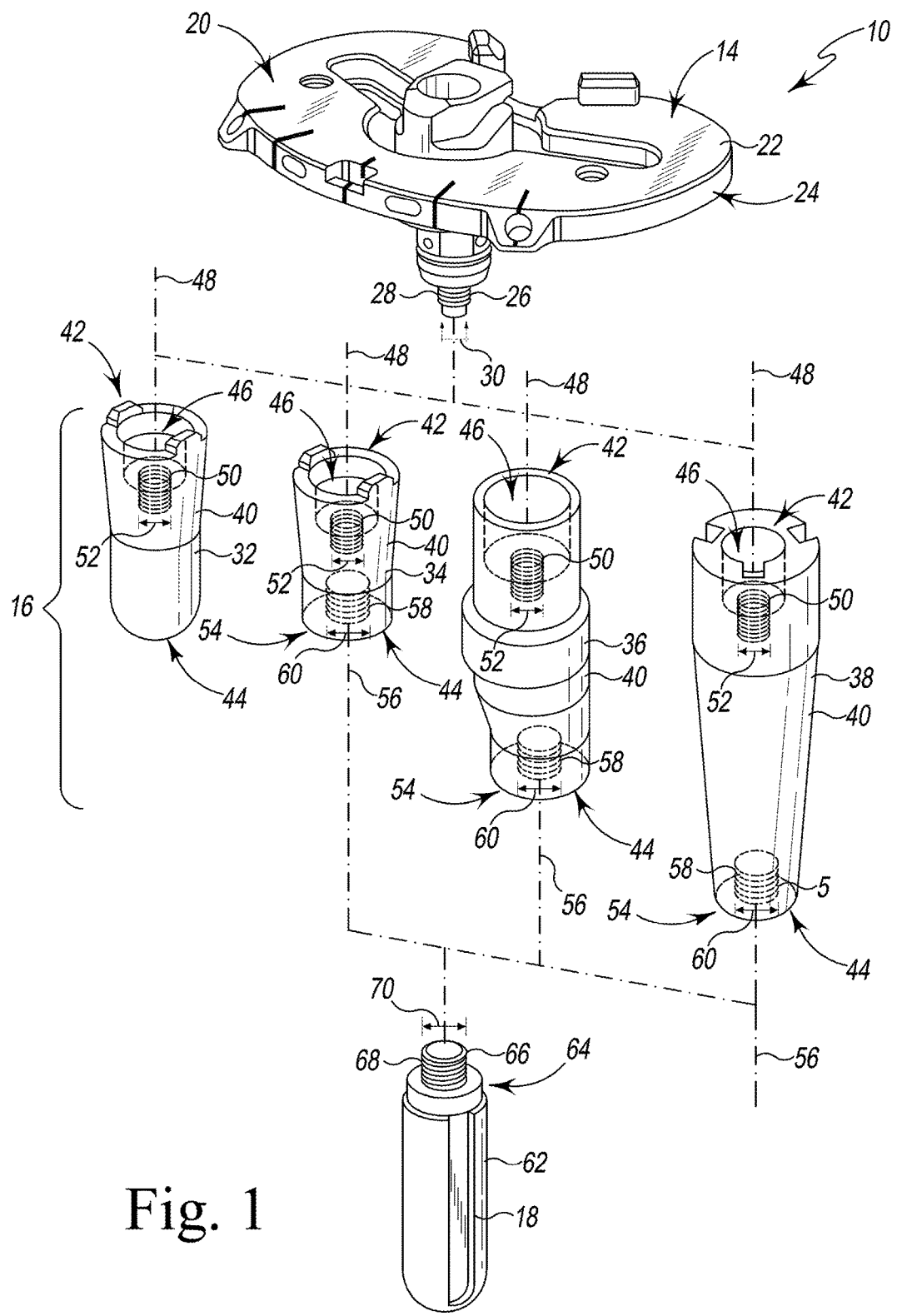
FIG. 1 is an exploded view of an orthopaedic prosthetic trial system having a tibial surface trial, intermediate trial components, and stem components.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 2:
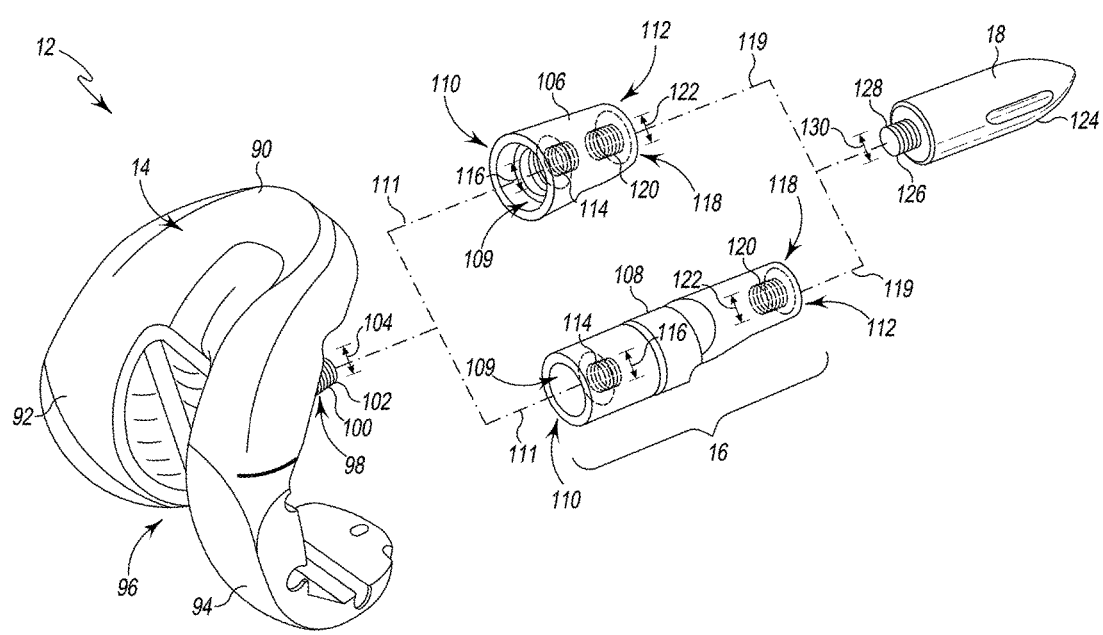
FIG. 2 is an exploded view of another orthopaedic prosthetic trial system having a femoral surface trial, intermediate trial components, and a stem component.
Figure 3:
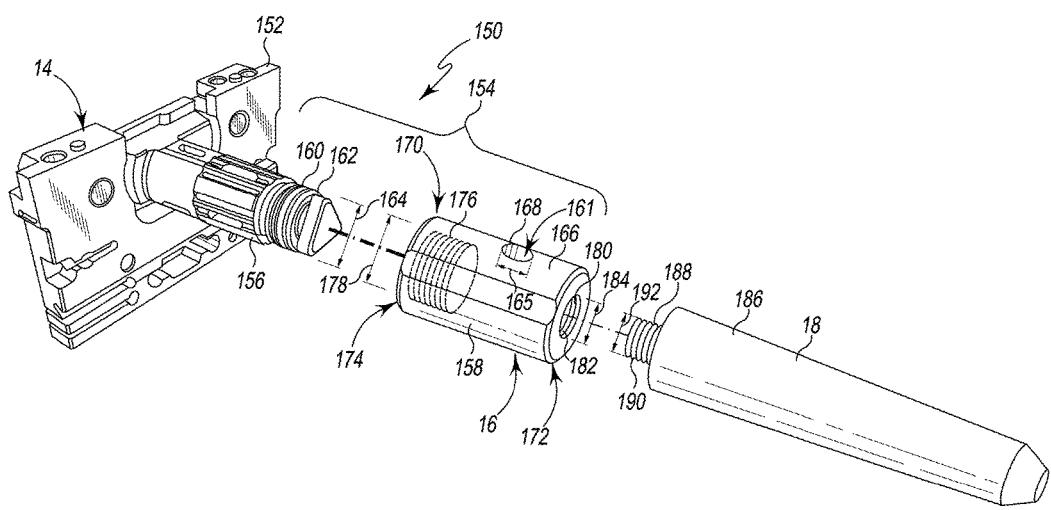
FIG. 3 is an exploded view of a femoral surgical system having a cutting block, an offset adaptor, a stem stabilizer, and a stem component.

Referring to FIGS. 1-3, a tibial trial system 10, a femoral trial system 12, and a femoral surgical system 150 may include various interchangeable components. Each system 10, 12, 150 includes a surface trial component 14 that is positioned directly on a surface of a bone, i.e. tibia or femur, respectively. An intermediate trial component 16 may be coupled directly to the surface trial component 14. Additionally, a stem trial component 18 is configured to couple to the intermediate trial component 16. Each of the components 14, 16, 18 is coupled utilizing threaded connectors. A diameter of the threaded connectors may vary depending on the type of component so that only compatible components are coupled to one another.

Often, during trialing of a tibial prosthetic and/or a femoral prosthetic at least some of the trial components 16, 18 may become inadvertently disassembled within the respective bone. The surgeon is then required to extract these components before continuing with the procedure. Because each of the components includes a different-sized connector, multiple tools may be required to extract components throughout a procedure. Additionally, the surgeon may encounter difficulty in extracting components because the surgeon is incapable of applying the required torque to extract the component.

Referring to FIG. 1, the tibial trial system 10 includes a tibial surface trial 20. In the exemplary embodiment, the tibial surface trial 20 is a fixed bearing tibial tray trial. In some embodiments, the tibial surface trial 20 may include any other tibial surface trial component, e.g. a rotating platform tibial tray trial. The tibial surface trial 20 includes a tibial tray 22 that is configured to be positioned on a surgically-prepared end of a patient's proximal tibia (not shown). The tibial tray 22 includes a platform 24 and a stem post 26 extending from the platform 24. The stem post 26 is configured to receive one of a number of different intermediate components 16. The stem post 26 includes male threads 28 having a diameter 30 of 5 millimeters. In some embodiments, the male threads 28 have a different diameter 30. An insert (not shown) is securable to the tibial tray 22. The insert may be snap-fit to the tibial tray 22. In such a way, the insert is fixed relative to the tibial tray 22 (i.e., it is not rotatable or moveable in the anterior/posterior or medial/lateral directions). Although, in other embodiments, the insert may be secured in a manner that allows it to rotate relative to the tibial tray 22. The insert includes lateral and medial articulation surfaces that are configured to articulate with the corresponding articulation surfaces of a femoral component.

A plurality of intermediate trial components 16 are interchangeably coupled to the tibial surface trial 20. In the illustrative embodiment, the plurality of intermediate trial components 16 includes a fixed bearing adaptor trial 32, a fixed bearing stem adaptor trial 34, a tibial offset adaptor trial 36, and a rotating platform stem adaptor trial 38. In other embodiments, the intermediate trial components 16 may be other trial components. The intermediate trial components 16 are configured to couple to the stem post 26. Each intermediate trial component 16 includes a body 40 having a proximal end 42 and a distal end 44. A bore 46 is formed in the proximal end 42 and extends along a longitudinal axis 48. The bore 46 includes female threads 50 having a diameter 52 of 5 millimeters. The female threads 50 are configured to thread to the stem post 26 of the tibial trial system 10. In some embodiments, the female threads 50 may have a different diameter 52.

A bore 54 is defined in the distal end 44 of each of the fixed bearing stem adaptor trial 34, the tibial offset adaptor trial 36, and the rotating platform stem adaptor trial 38 along a longitudinal axis 56. The bore 54 includes female threads 58 having a diameter 60 of 8 millimeters. In some embodiments, the female threads 58 may have a different diameter 60. The longitudinal axis 48 of the bore 46 and the longitudinal axis 56 of the bore 54 extend collinear in the fixed bearing stem adaptor trial 34 and the rotating platform stem adaptor trial 38. The longitudinal axis 48 of the bore 46 and the longitudinal axis 56 of the bore 54 are offset and extend parallel in the tibial offset adaptor trial 36.

A tibial stem trial 62 interchangeably couples to one of the fixed bearing stem adaptor trial 34 and the tibial offset adaptor trial 36. The tibial stem trial 62 is configured to couple to the female thread 58 of the bore 54 of one of the fixed bearing stem adaptor trial 34, the tibial offset adaptor trial 36, or the rotating platform stem adaptor trial 38. The tibial stem trial 62 includes a proximal end 64 having a threaded post 66. The threaded post 66 includes male threads 68 having a diameter 70 of 8 millimeters. In some embodiments, the male threads 68 may have a different diameter 70. The male threads 68 of the tibial stem trial 62 are configured to thread to the female threads 58 of one of the intermediate trial components 16.

Referring to FIG. 2, the femoral trial system 12 includes a femoral surface trial 90. In some embodiments, the femoral surface trial 90 may include any other femoral surface component, e.g. a femoral cut-through trial. The femoral surface trial 90 includes a medial condyle 92 spaced apart from a lateral condyle 94. The medial condyle 92 and the lateral condyle 94 are sized and shaped to articulate on a bearing surface of a tibial trial component (not shown). An intercondylar notch 96 is positioned between the medial condyle 92 and the lateral condyle 94. A passageway (not shown) opens into the intercondylar notch 96 and extends through the femoral surface trial 90. A stem trial bolt 98 is positioned in the passageway so that a threaded shaft 100 of the stem trial bolt 98 extends from the femoral surface trial 90. The threaded shaft 100 includes male threads 102 having a diameter 104 of 8 millimeters. In other embodiments, the male threads 102 may have a different diameter 104.

Intermediate trial components 16 are configured to interchangeably couple to the femoral surface trial 90. In the illustrative embodiment, the intermediate trial components 16 include a boss adaptor trial 106 and a femoral offset adaptor trial 108. In other embodiments, the intermediate trial components 16 may be other intermediate trial components. The intermediate trial components 16 include a proximal end 110 and a distal end 112. A bore 109 is defined in the proximal end 110 along a longitudinal axis 111. The bore 109 includes female threads 114 having a diameter 116 of 8 millimeters. In some embodiments, the female threads 114 may have a different diameter 116. The female threads 114 are configured to thread to the male threads 102 of the threaded shaft 100 of the femoral surface trial 90. A bore 118 is defined in the distal end 112 of each intermediate trial component 16 along a longitudinal axis 119. The bore 118 includes female threads 120 having a diameter 122 of 8 millimeters. In some embodiments, the female threads 120 have a different diameter 122. In the boss adaptor trial 106, the longitudinal axis 111 extends collinear with the longitudinal axis 119. In the femoral offset adaptor trial 108, the longitudinal axis 111 is offset from and extends parallel to the longitudinal axis 119.

A femoral stem trial 124 interchangeably couples to one of the intermediate trial components 16. It should be appreciated that in some embodiments, the femoral stem trial 124 may be the same as the tibial stem trial 62. The femoral stem trial 124 includes a threaded post 126 having male threads 128 with a diameter 130 of 8 millimeters. In some embodiments, the male threads 128 have a different diameter 130. The male threads 128 are configured to thread to the female threads 120 of the intermediate trial component 16.

Referring to FIG. 3, a femoral surgical system 150 includes a base cutting block 152 configured for use on surgically-prepared surface of a patient's femur. An intramedullary adaptor 154 is configured to be secured to the base cutting block 152. In the illustrative embodiment, the intramedullary adaptor is an "intramedullary orthopedic surgical instrument," which is a surgical tool configured to be at least partially positioned in the medullary canal of the patient's femur during the orthopedic surgical procedure. The intramedullary adaptor 154 includes a guide 156 and a stem stabilizer 158 configured to be attached to a stem trial 18. It should be appreciated that an assembly including the guide 156 and the stem stabilizer 158 without the stem trial may be an intramedullary orthopedic surgical instrument; similarly, an assembly including the stem stabilizer 158 and the stem trial 18 may be an intramedullary orthopedic surgical instrument.

A threaded post 160 extends from the intramedullary adaptor 154. The threaded post 160 includes male threads 162 having a diameter 164 of 12 millimeters. In some embodiments, the male threads 162 may have a different diameter 164. The stem stabilizer 158 is configured to couple to the threaded post 160. The stem stabilizer 158 includes a proximal end 170 and a distal end 172. A bore 174 is defined in the proximal end 170. The bore 174 has female threads 176 with a diameter 178 of 12 millimeters. In some embodiments, the female threads 176 may have a different diameter 178. The female threads 176 are configured to couple to the male threads 162 of the threaded post 160. A bore 180 is defined in the distal end 172 of the stem stabilizer 158. The bore 180 includes female threads 182 having a diameter 184 of 8 millimeters. In some embodiments, the female threads 182 have a different diameter 184.

The stem stabilizer 158 includes an outer sidewall 166. An opening 161 is defined in the outer sidewall 166 and is aligned with an opposite opening (not shown) that is formed in the outer sidewall 166. The openings from a bore 168 having a diameter 165.

A femoral stem trial 186 is configured to couple to the distal end 172 of the stem stabilizer 158. It should be appreciated that in some embodiments, the femoral stem trial 186 may be the same as the femoral stem trial 124 and/or the tibial stem trial 62. The femoral stem trial 186 includes a threaded post 188. The threaded post 188 includes male threads 190 having a diameter 192 of 8 millimeters. In some embodiments, the male threads 190 have a different diameter 192. The male threads 190 are configured to thread to the female threads 182 of the stem stabilizer 158.

Figure 4:
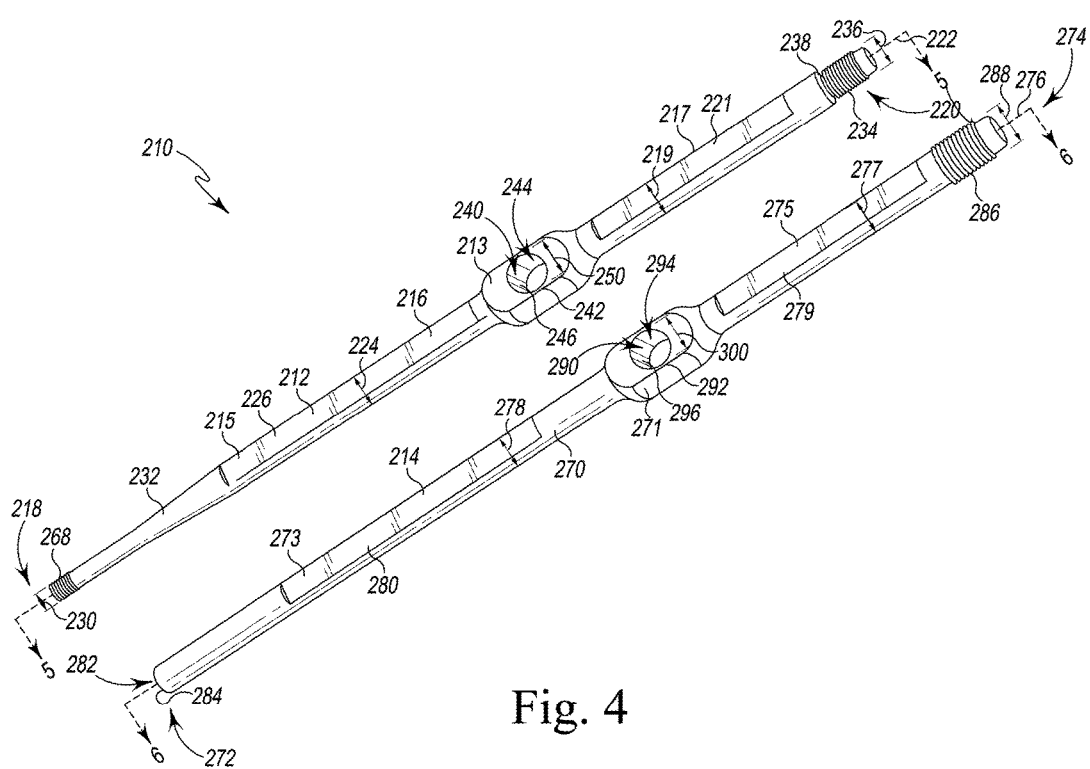
FIG. 4 is a perspective view of a surgical instrument extraction system.

Referring to FIG. 4, a surgical instrument extraction system 210 is provided for extracting intermediate trial components 16 and stem trial components 18. The surgical instrument extraction system 210 includes a multiple adaptor trial extraction tool 212 and a multi-instrument extraction tool 214. The multiple adaptor trial extraction tool 212 and the multi-instrument extraction tool 214 may be formed from metal. In some embodiments, the multiple adaptor trial extraction tool 212 and the multi-instrument extraction tool 214 may be formed any suitable surgical grade material. The extraction tool 212 has a body 216 extending between a first end 218 and a second end 220 along a longitudinal axis 222. A central body 213 is positioned between the first end 218 and the second end 220. A pair of openings 240 and 242 are formed in the central body 213. A cylindrical sidewall 246 extends through the central body 213 between the openings 240 and 242. The openings 240 and 242 and the cylindrical sidewall 246 cooperate to form a bore 244 in the central body 213. The bore 244 has a diameter 250.

A first shaft 215 having a diameter 224 extends between the central body 213 and the first end 218. The first shaft 215 includes a flat surface 226 that may be configured to receive indicia to indicate what components correspond to the first end 218. For example, the flat surface 226 may include indicia indicating that the first end 218 corresponds with an intermediate trial component 16 of the tibial trial system 10. In some embodiments, the flat surface 226 may include a part number or other similar part indicator. The flat surface 226 also prevents the extraction tool 212 from rolling, e.g. when placed on a table. A frutso-conical section 232 extends from the first shaft 215 and tapers toward the longitudinal axis 222 from the first shaft 215 to the first end 218. A threaded post 268 extends from the first end 218. The threaded post 268 extends from a cylindrical section extending from the frusto-conical section 232. The threaded post 268 is configured to selectively couple to the fixed bearing adaptor trial 32, the fixed bearing stem adaptor trial 34, the tibial offset adaptor trial 36, and the rotating platform stem adaptor trial 38. The threaded post 268 has a diameter 230 that is less than the diameter 224.

A second shaft 217 having a diameter 219 extends between the central body 213 and the second end 220. The diameter 219 is equal to the diameter 224 of the first shaft 215. The second shaft 217 includes a flat surface 221 that may be configured to receive indicia to indicate what components correspond to the second end 220. For example, the flat surface 221 may include indicia indicating that the second end 220 corresponds with an intermediate trial component 16 of the femoral trial system 12. In some embodiments, the flat surface 221 may include a part number or other similar part indicator. The flat surface 221 also prevents the extraction tool 212 from rolling, e.g. when placed on a table. A threaded post 234 extends from the second end 220. The threaded post 234 is configured to selectively couple to the boss adaptor trial 106 and the femoral offset adaptor trial 108. The threaded post 234 has a diameter 236 that is less than the diameter 219 of the second shaft 217. The second shaft 217 steps down to the threaded post 234 at a flange 238. The flange 238 extends circumferentially around the threaded post 234 and forms a surface that engages the boss adaptor trial 106 and/or the femoral offset adaptor trial 108 when the boss adaptor trial 106 and/or the femoral offset adaptor trial 108, respectively, are fully secured to the threaded post 234.

As set forth above, surgical instrument extraction system 210 also includes the extraction tool 214. The extraction tool 214 has a body 270 extending between a first end 272 and a second end 274 along a longitudinal axis 276. A central body 271 is positioned between the first end 272 and the second end 274. A pair of openings 290 and 292 are formed in the central body 271. A cylindrical sidewall 296 extends through the central body 271 between the openings 290 and 292. The openings 290 and 292 and the cylindrical sidewall 296 cooperate to form a bore 294 in the central body 271. The bore 294 has a diameter 300.

A first shaft 273 having a diameter 278 extends between the central body 271 and the first end 272. The first shaft 273 includes a flat surface 280 that may be configured to receive indicia to indicate what components correspond to the first end 272. For example, the flat surface 280 may include indicia indicating that the first end 272 corresponds with a stem component 18. In some embodiments, the flat surface 280 may include a part number or other similar part indicator. The flat surface 280 also prevents the extraction tool 214 from rolling, e.g. when placed on a table. A bore 282 is defined in the first end 272 and is configured to selectively couple to the tibial stem trial 62, the femoral stem trial 124, and the femoral stem trial 186. An outer end surface 284 extends around the bore 282. The outer end surface 284 engages the tibial stem trial 62, the femoral stem trial 124, and/or the femoral stem trial 186 when the tibial stem trial 62, the femoral stem trial 124, and/or the femoral stem trial 186, respectively, are fully secured to the first end 272.

A second shaft 275 having a diameter 277 extends between the central body 271 and the second end 274. The diameter 277 is equal to the diameter 278. The second shaft 275 includes a flat surface 279 that may be configured to receive indicia to indicate what components correspond to the second end 274. For example, the flat surface 279 may include indicia indicating that the second end 274 corresponds with the stem stabilizer 158. In some embodiments, the flat surface 279 may include a part number or other similar part indicator. The flat surface 279 also prevents the extraction tool 214 from rolling, e.g. when placed on a table. A threaded post 286 extends from the second shaft 275 and is configured to couple to the stem stabilizer 158. The threaded post 286 has a diameter 288 that is greater than the diameter 278.

The diameter 300 of the bore 294 of extraction tool 214 is greater than the diameters 224 of the first shaft 215 and the diameter 219 of the second shaft 217 of extraction tool 212. Accordingly, the first shaft 215 and the second shaft 217 of the extraction tool 212 may be received within the bore 294 of the extraction tool 214 to provide torque to the extraction tool 214. The diameter 250 of the bore 244 of extraction tool 212 is greater than the diameter 278 of the first shaft 273 of the extraction tool 214 but less than the diameter 288 of the threaded post 286 of the extraction tool 214. Accordingly, the first shaft 273 of the extraction tool 214 may be received within the bore 244 of the extraction tool 212 to provide torque to the extraction tool 212.

Figure 5:
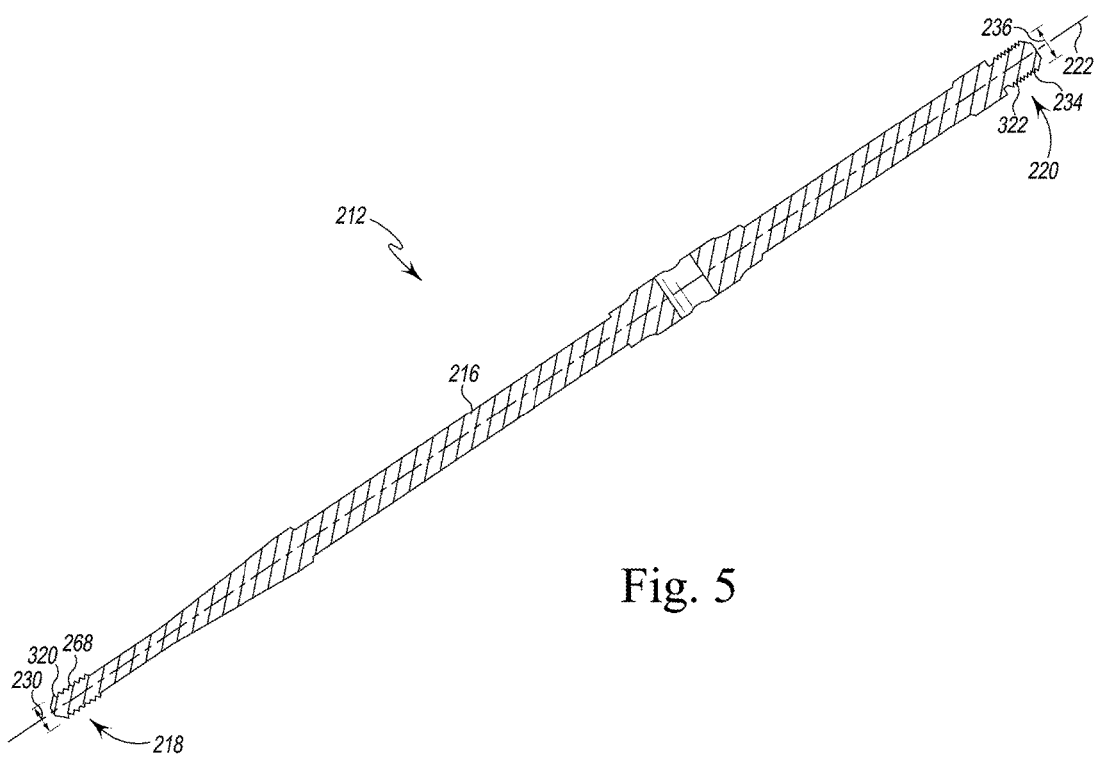
FIG. 5 is a cross-sectional view of a multiple adaptor extraction tool of the surgical instrument extraction system shown in FIG. 4 taken along line 5-5.

Referring to FIG. 5, the threaded post 268 of the extraction tool 212 includes male threads 320 having diameter 230 of 5 millimeters. In some embodiments, the male threads 320 have a different diameter 230. The male threads 320 are sized and shaped to connect to the female threads 50 of the tibial intermediate trial components 16, e.g. the fixed bearing adaptor trial 32, the fixed bearing stem adaptor trial 34, the tibial offset adaptor trial 36, and the rotating platform stem adaptor trial 38. The threaded post 234 of the extraction tool 212 includes male threads 322 having diameter 236. In some embodiments, the diameter 236 is 8 millimeters, but the male threads 322 may have a different diameter 236. The male threads 322 are sized and shaped to couple to the female threads 114 of the femoral intermediate trial components 16, e.g. the boss adaptor trial 106 and the femoral offset adaptor trial 108.

Figure 6:
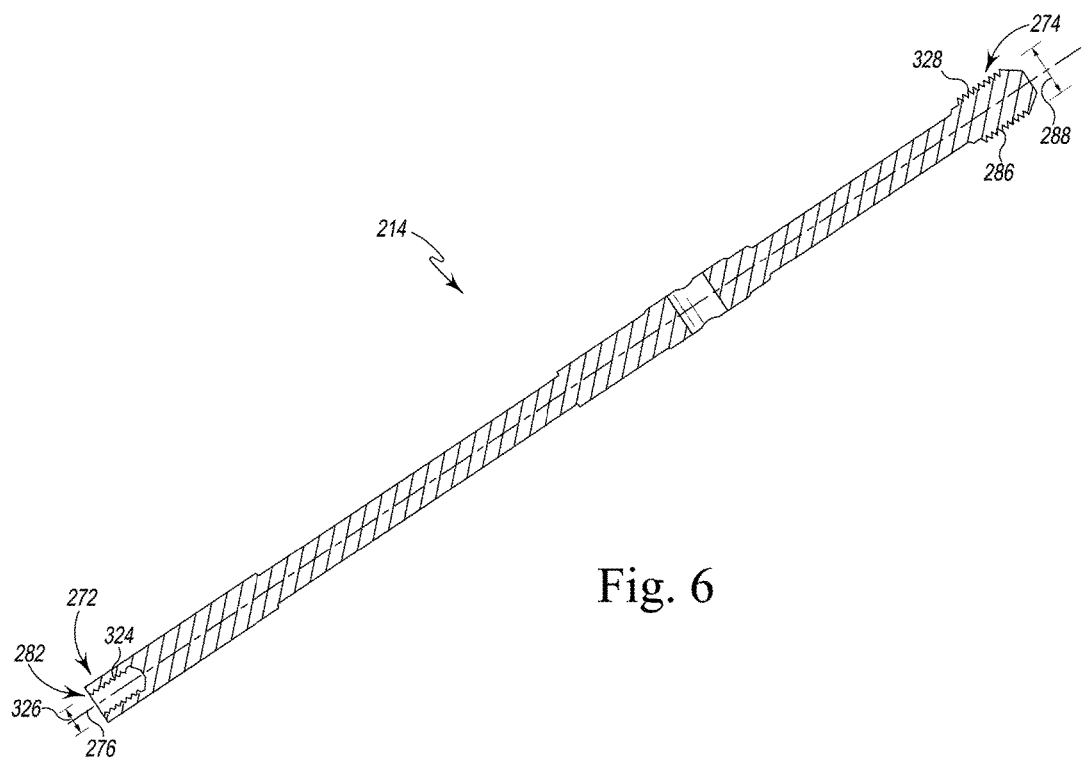
FIG. 6 is a cross-sectional view of a multi-instrument trial extraction tool of the surgical instrument extraction system shown in FIG. 4 taken along line 6-6.

Referring to FIG. 6, the bore 282 of the extraction tool 214 includes female threads 324 having a diameter 326 of 8 millimeters. In some embodiments, the female threads 324 have a different diameter 326. The female threads 324 are sized and shaped to thread to the threaded post 66 of the tibial stem trial 62, the threaded post 126 of the femoral stem trial 124, and the threaded post 188 of the femoral stem trial 186. The threaded post 286 includes male threads 328 having diameter 288. In some embodiments, the diameter 288 is 12 millimeters, but the male threads 328 may have a different diameter 288. The male threads 328 are sized and shaped to connect to the female threads 176 of the stem stabilizer 158.

Figure 7:
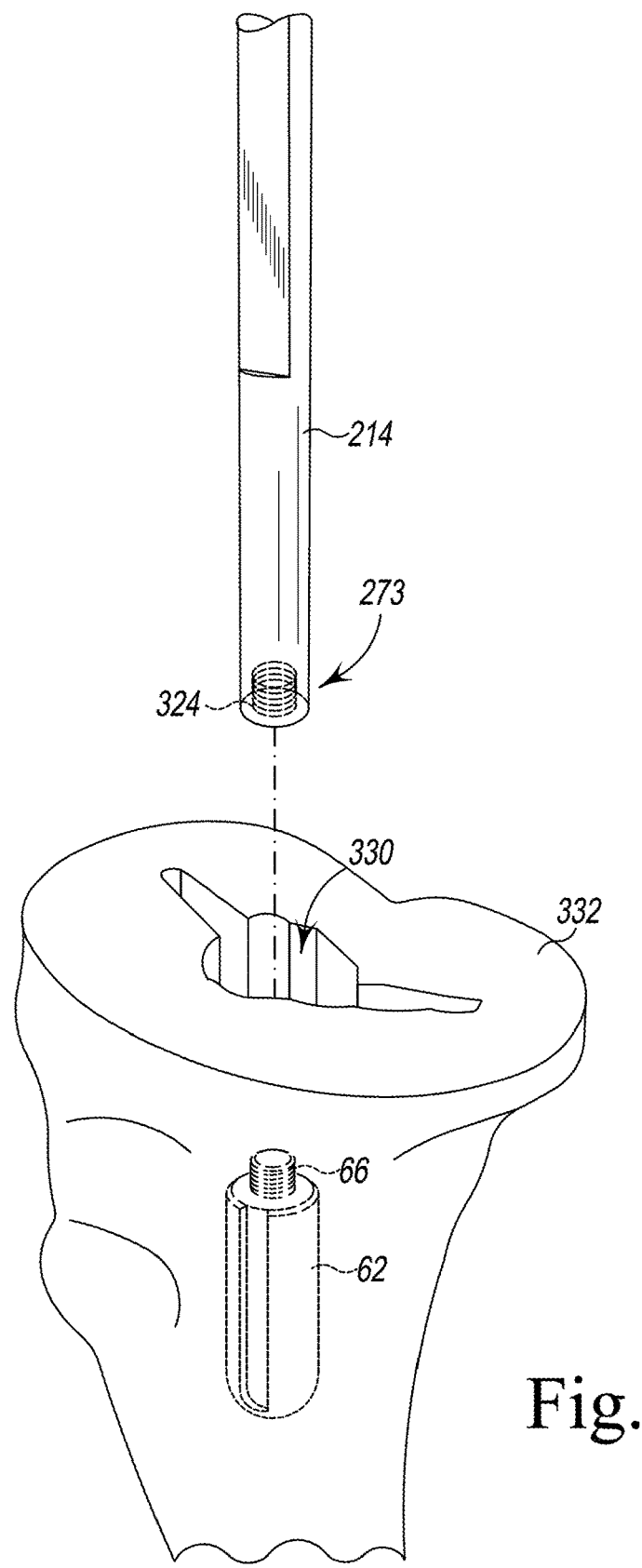
FIG. 7 is a perspective view of the multi-instrument trial extraction tool shown in FIG. 4 being inserted into a bone to extract a stem component.
Figure 8:
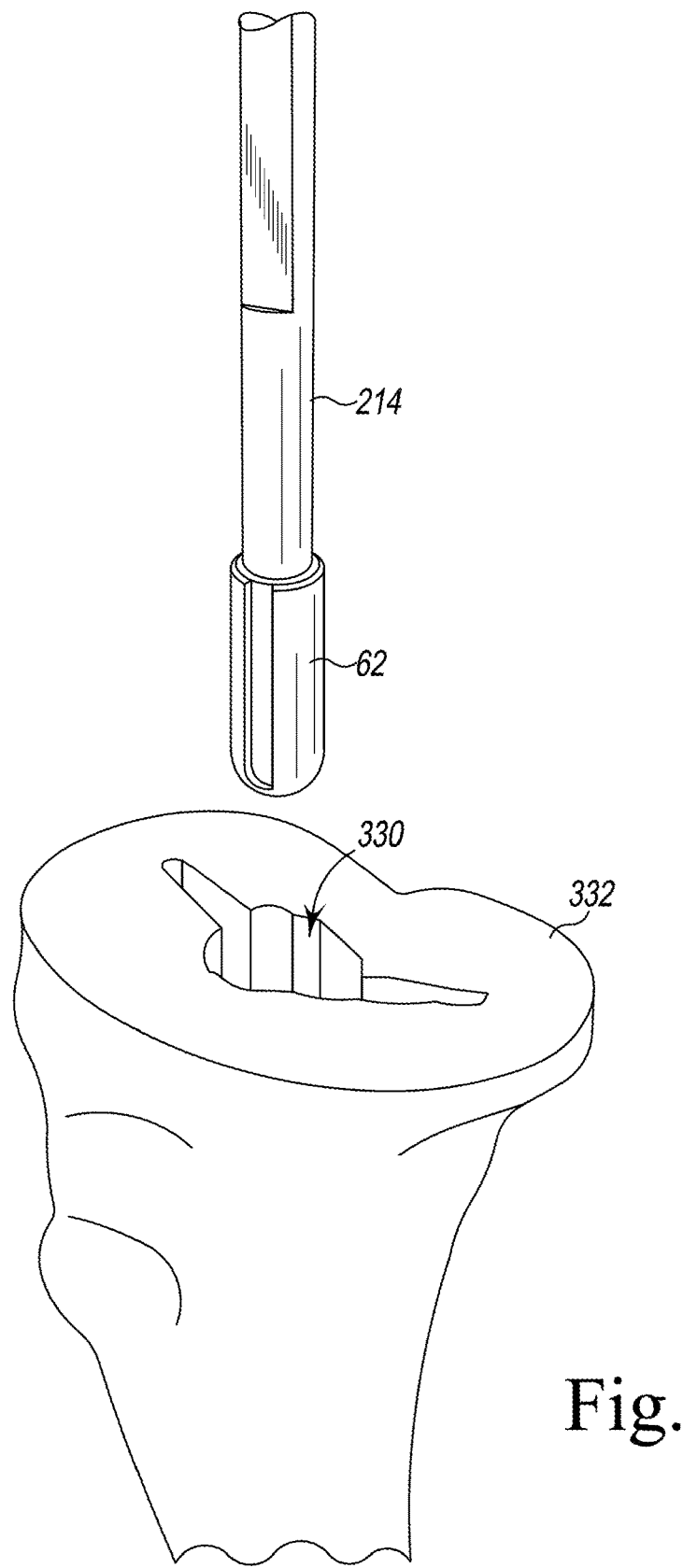
FIG. 8 is a perspective view similar to FIG. 7 showing the stem component extracted from the bone.

Referring to FIG. 7, during joint arthroplasty, a tibial stem trial 62 may become inadvertently disassembled within a cavity 330 of a tibial bone 332. To remove the tibial stem trial, a surgeon or other user advances the first shaft 273 of the extraction tool 214 into the cavity 330 such that the female threads 324 thread to the threaded post 66 of the tibial stem trial 62. The surgeon then applies leverage to the extraction tool 214 to remove the tibial stem trial 62 from the bone 332, as illustrated in FIG. 8. It will be appreciated that in a similar fashion the first shaft 273 of the extraction tool 214 may be utilized to extract any one of the femoral stem trial 124 and/or the femoral stem trial 186 from a bone.

Figure 9:
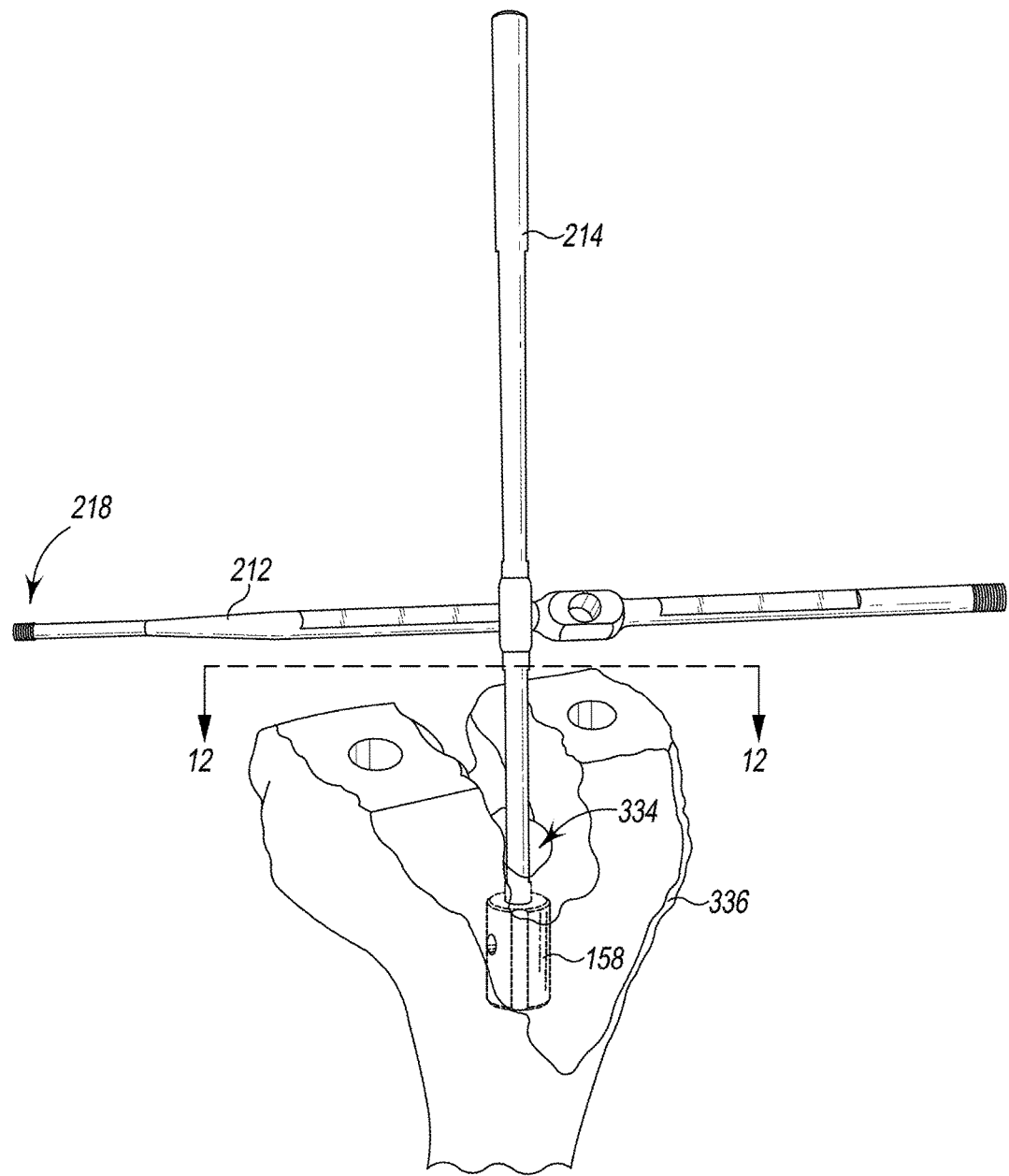
FIG. 9 is a perspective view of the multiple adaptor trial extraction tool shown in FIG. 4 attached to the multi-instrument extraction tool shown in FIG. 4.
Figure 12:
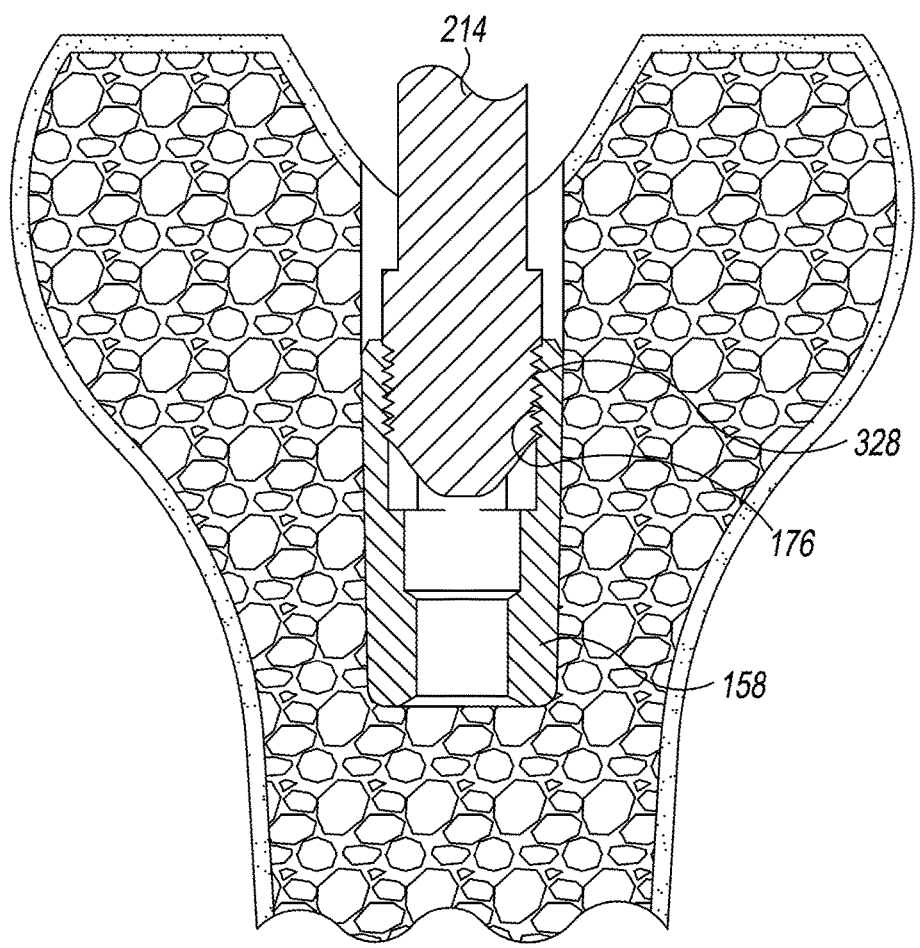
FIG. 12 is a cross-sectional view of the multi-instrument extraction tool coupled to the stem stabilizer taken along line 12-12 shown in FIG. 9.

Referring to FIG. 9, during joint arthroplasty, the stem stabilizer 158 may become inadvertently disassembled within a cavity 334 of a femoral bone 336. It will be appreciated that while only the stem stabilizer 158 is illustrated within the femoral bone 336, the femoral stem trial 186 would also be coupled to the stem stabilizer 158. Accordingly, the extraction process described below may include the extraction of the stem stabilizer 158 with the femoral stem trial 186 coupled to the stem stabilizer 158. To remove the stem stabilizer 158, the surgeon or other user advances the second shaft 275 of the extraction tool 214 into the cavity 334 to retrieve the stem stabilizer 158. The male threads 328 of the extraction tool 214 are threaded onto the female threads 176 of the stem stabilizer 158 (as shown in FIG. 12) so that the extraction tool 212 can provide leverage, e.g. torque, to remove the stem stabilizer 158 from the bone 336. Before applying leverage, the surgeon may then insert the first shaft 215 of the extraction tool 212 within the bore 294 of the extraction tool 214. Notably, the second shaft 217 may also be inserted into the bore 294 of the extraction tool 214. By coupling the extraction tools 212 and 214, the extraction tool 212 forms a crossbar for the extraction tool 214. The crossbar configuration enables the surgeon to apply leverage to the extraction tool 214 to aid the surgeon in removing the stem stabilizer 158 from the bone 336. It should be noted that other surgical instruments may be inserted into the bore 294 to form a crossbar for additional torque.

Figure 10:
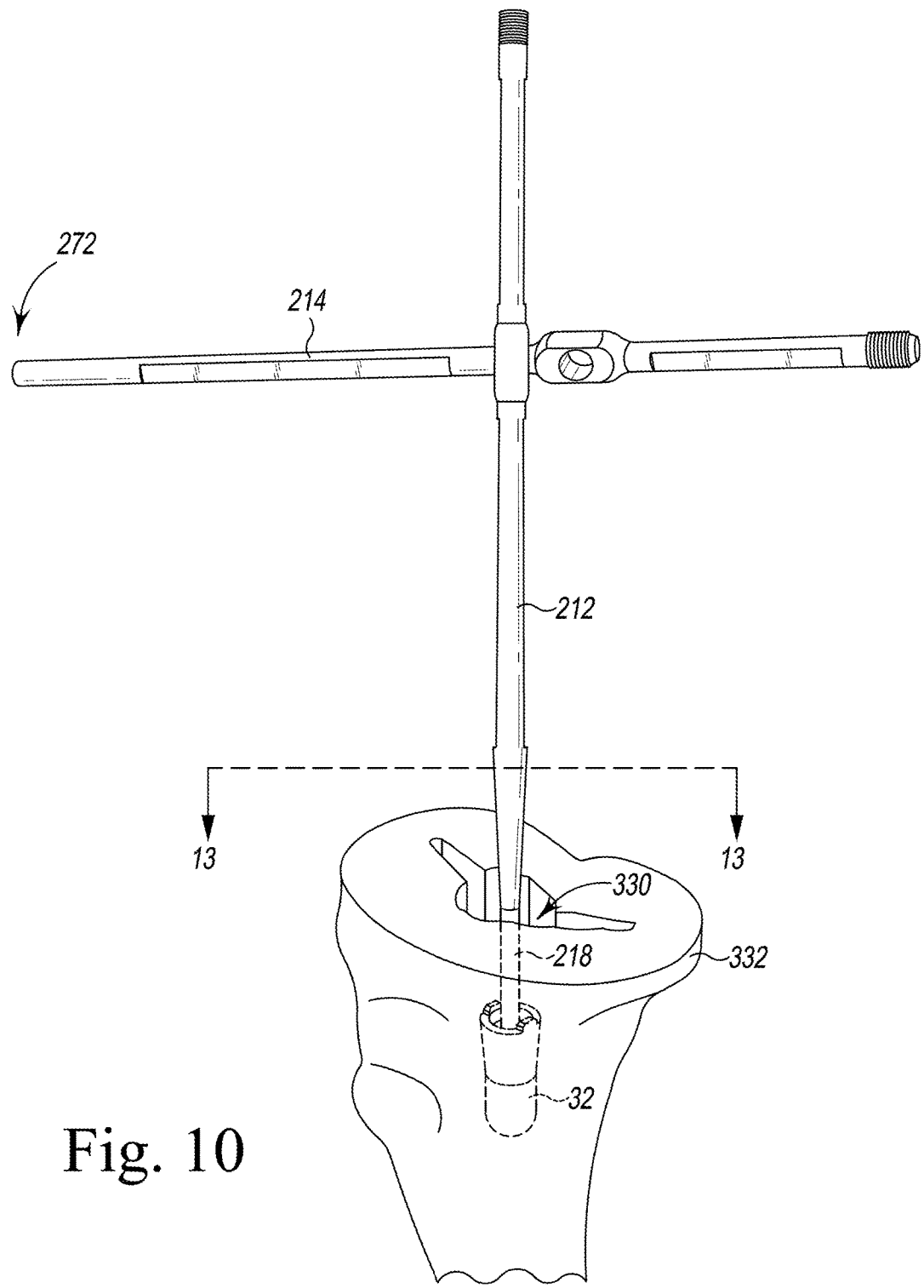
FIG. 10 is a perspective view of the multi-instrument extraction tool shown in FIG. 4 attached to the multiple adaptor trial extraction tool shown in FIG. 4.
Figure 13:
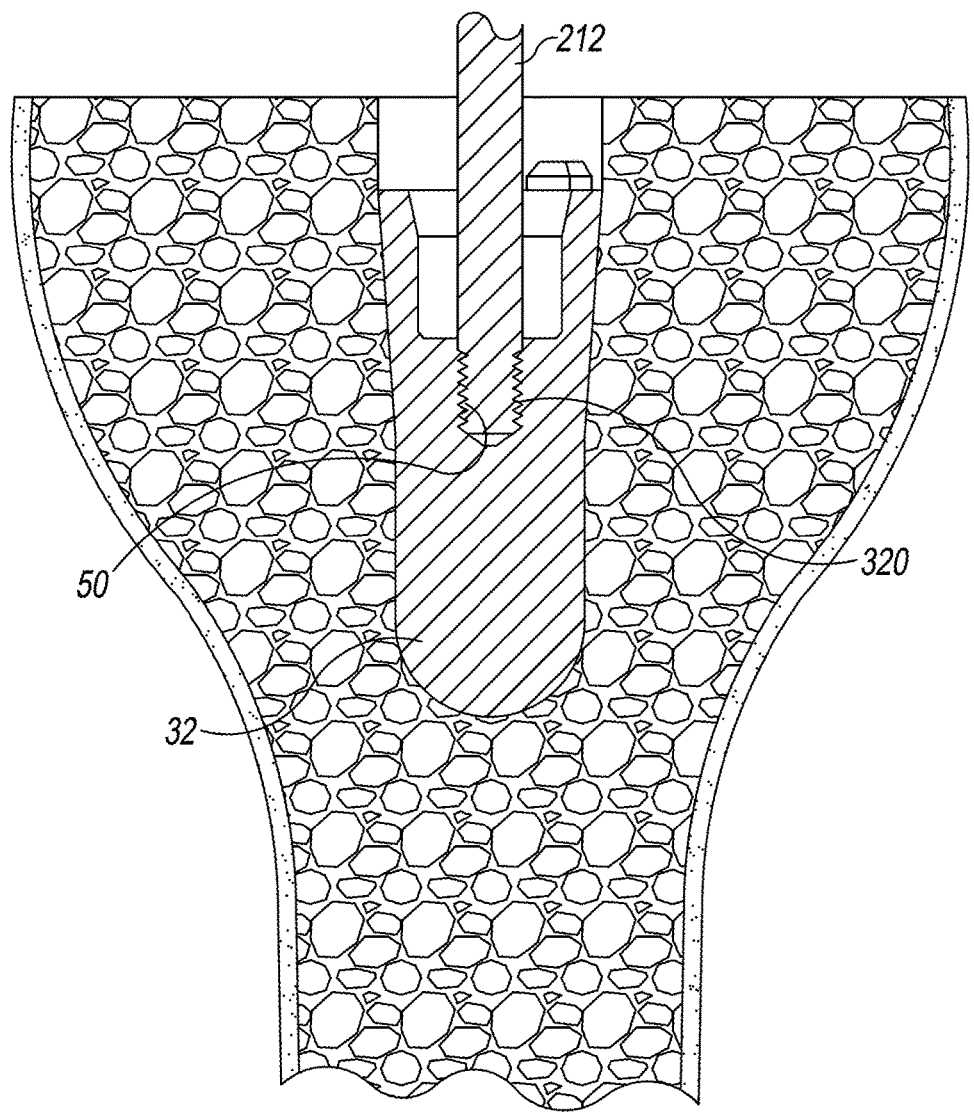
FIG. 13 is a cross-sectional view of the multiple adaptor extraction tool coupled to an intermediate tibial trial component taken along line 13-13 shown in FIG. 10.

Referring to FIG. 10, during joint arthroplasty, a fixed bearing adaptor trial 32 may become inadvertently disassembled within the cavity 330 of the tibial bone 332. To remove the fixed bearing adaptor trial 32, the surgeon or other user advances the first shaft 215 of the extraction tool 212 into the cavity 330 to retrieve the fixed bearing adaptor trial 32. The male threads 320 engage the female threads 50 of the fixed bearing adaptor trial 32 (as shown in FIG. 13) so that the extraction tool 212 can provide leverage, e.g. torque, to remove the fixed bearing adaptor trial 32 from the bone 332. Before applying leverage, the surgeon may then position the first shaft 273 of the extraction tool 214 in the bore 244 of the extraction tool 212 to couple the extraction tools 212 and 214. By coupling the extraction tools 212 and 214, the extraction tool 214 forms a crossbar for the extraction tool 212. The crossbar configuration enables the surgeon to apply leverage to the extraction tool 212 to aid the surgeon removing the fixed bearing adaptor trial 32 from the bone 332. It will be appreciated that in a similar fashion the first shaft 215 of the extraction tool 212 may be utilized to extract any one of the fixed bearing stem adaptor trial 34, the tibial offset adaptor trial 36, and the rotating platform stem adaptor trial 38 from a bone.

Figure 11:
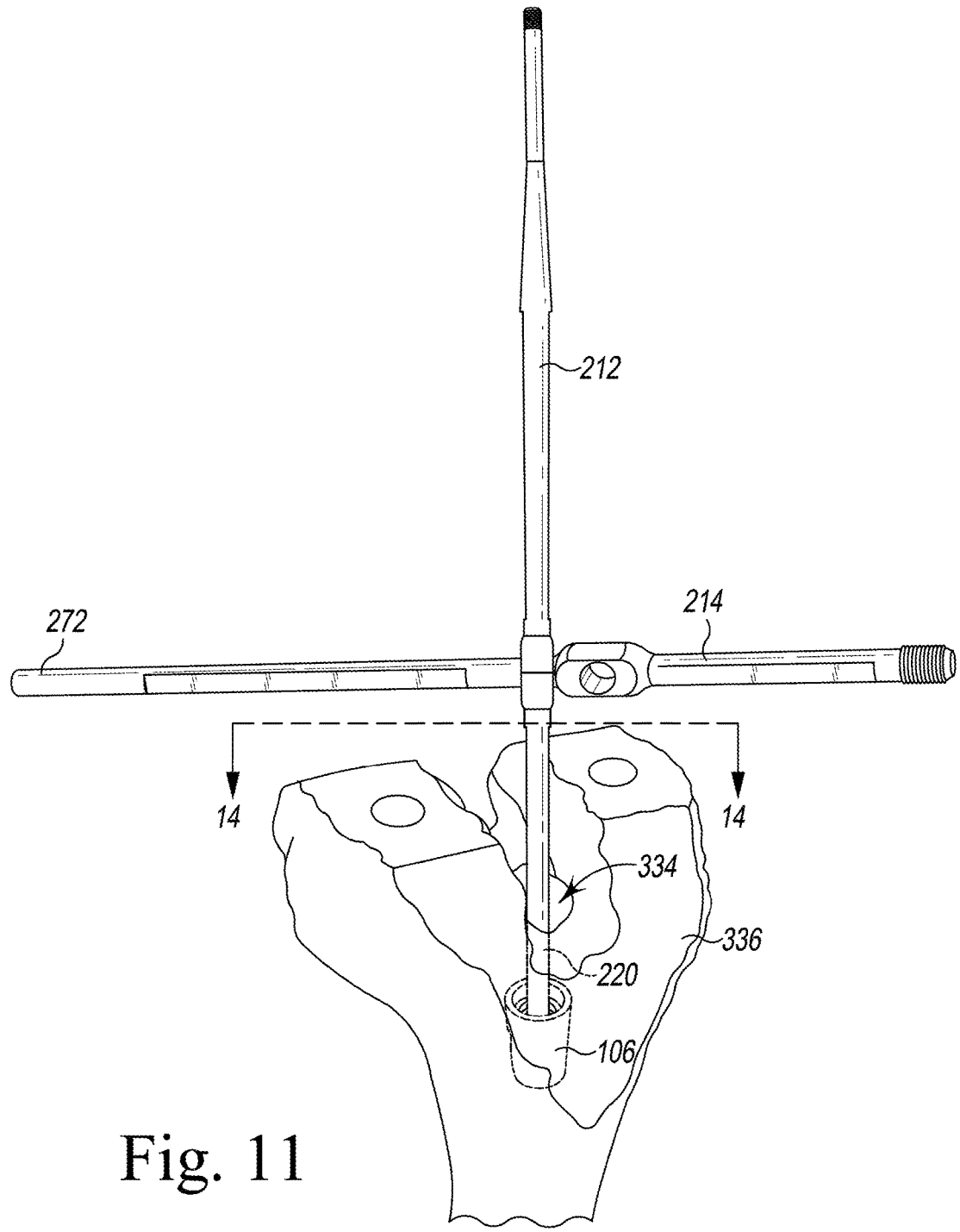
FIG. 11 is a perspective view of the multi-instrument extraction tool shown in FIG. 4 attached to the multiple adaptor trial extraction tool shown in FIG. 4.
Figure 14:
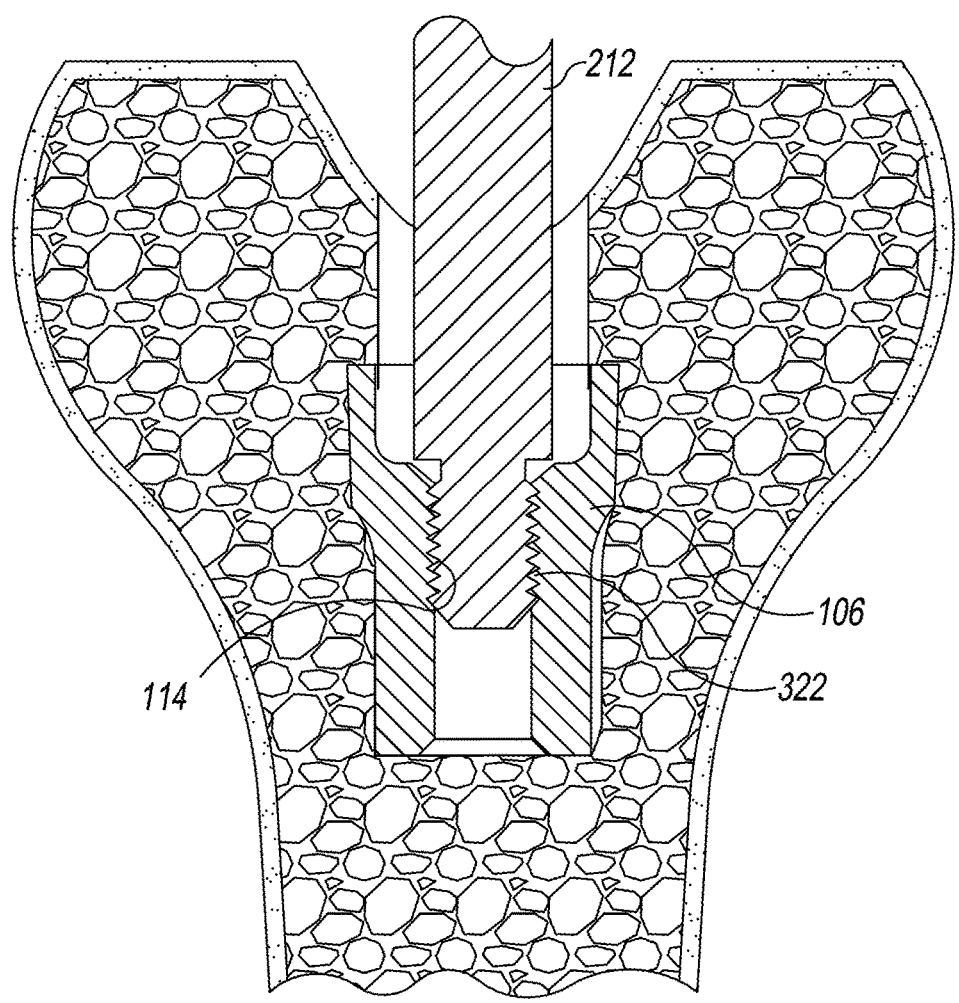
FIG. 14 is a cross-sectional view of the multiple adaptor trial extraction tool coupled to an intermediate femoral trial component taken along line 14-14 shown in FIG. 11.

Referring to FIG. 11, during joint arthroplasty, a boss adaptor trial 106 may become inadvertently disassembled within the cavity 334 of the femoral bone 336. It will be appreciated that while only the boss adaptor trial 106 is illustrated within the femoral bone 336, the femoral stem trial 124 would also be coupled to the boss adaptor trial 106. Accordingly, the extraction process described below may include the extraction of the boss adaptor trial 106 with the femoral stem trial 124 coupled to the boss adaptor trial 106. To remove the boss adaptor trial 106, the surgeon other user advances the second end 220 of the extraction tool 212 into the cavity 334 to retrieve the boss adaptor trial 106. The male threads 322 engage the female threads 114 of the boss adaptor trial 106 (as shown in FIG. 14) so that the extraction tool 214 can provide leverage, e.g. torque, to remove the boss adaptor trial 106 from the bone. Before applying leverage, the surgeon may then advance the first shaft 273 of the extraction tool 214 into the bore 244 of the extraction tool 212 to couple the extraction tools 212 and 214. By coupling the extraction tools 212 and 214, the extraction tool 214 forms a crossbar for the extraction tool 212. The crossbar configuration enables the surgeon to apply leverage to the extraction tool 212 to aid the surgeon in removing the boss adaptor trial 106 from the bone 336. It will be appreciated that in a similar fashion the second end 220 of the extraction tool 212 may be utilized to extract the femoral offset adaptor trial 108 from a bone.

Figure 15:
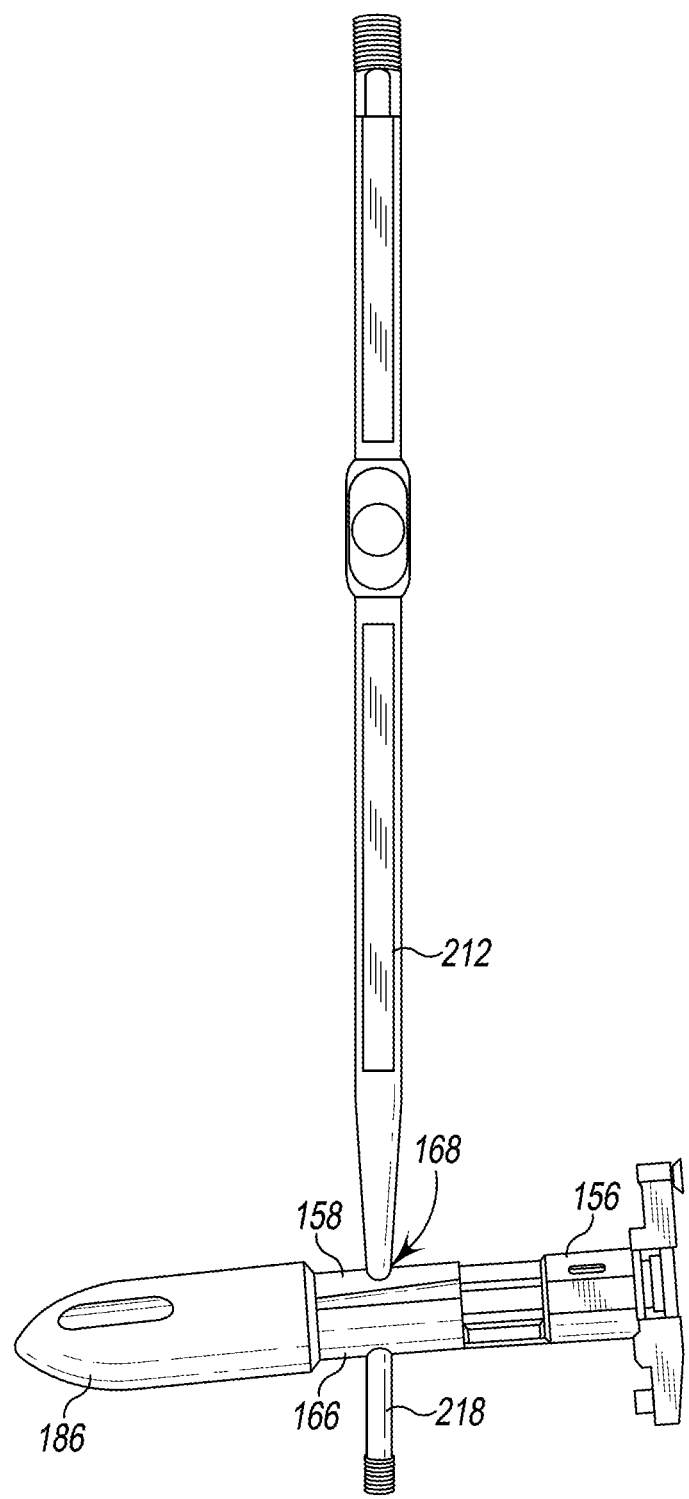
FIG. 15 is a perspective view of the multiple adaptor extraction tool shown in FIG. 4 coupled to the stem stabilizer shown in FIG. 3.

Referring to FIG. 15, the first end 218 of the extraction tool 212 is sized and shaped to be inserted into the bore 168 defined in the sidewall 166 of the stem stabilizer 158. The extraction tool 212 is inserted into the bore 168 of the stem stabilizer 158 to facilitate removing the stem stabilizer 158 from the intramedullary adaptor 154. That is, a surgeon or other user may grip the extraction tool 212 to retain the stem stabilizer 158 while the intramedullary adaptor 154 is rotated to separate the stem stabilizer 158 and the intramedullary adaptor 154. Likewise, the extraction tool 212 may be gripped by the surgeon to retain the stem stabilizer 158 while the femoral stem trial 186 is rotated to separate the femoral stem trial 186 and the stem stabilizer 158.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although the orthopaedic surgical instruments have been shown and described in reference to extracting tibial and femoral trial components, it should be appreciated that the orthopaedic surgical instruments may be used to extract or detach trial components from other joints of a patient's bone such as, for example, the hip, shoulder, or ankle joints.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A surgical instrument extraction system comprising:
a first extraction tool having a first body that extends between a first end and a second end, the first extraction tool having (i) a first plurality of threads formed on the first end and sized and shaped to selectively couple to a threaded end of a stem component of a femoral trial system and a stem component of a tibial trial system, (ii) a second plurality of threads formed on the second end and sized and shaped to selectively couple to a stem stabilizer of a femoral intramedullary adaptor, and (iii) a first bore extending through the body between a first side of the first body and a second side of the first body, and
a second extraction tool having a second body that extends between a first end having a first diameter and a second end having a second diameter greater than the first diameter, the second extraction tool having (i) a first plurality of threads formed on the first end and sized and shaped to selectively couple to an intermediate trial component of a tibial trial system, (ii) a second plurality of threads formed on the second end and sized and shaped to selectively couple to an intermediate trial component of a femoral trial system, and (iii) a second bore extending through the second body between a first side of the second body and a second side of the second body,
wherein the first body of the first extraction tool is sized to extend through the second bore of the second extraction tool to couple the first extraction tool to the second extraction tool to provide leverage to the second extraction tool to aid in extraction, and
wherein the second body of the second extraction tool is sized to extend through the first bore of the first extraction tool to couple the second extraction tool to the first extraction tool to provide leverage to the first extraction tool to aid in extraction.

2. The surgical instrument extraction system of claim 1, wherein:
the first plurality of threads of the first extraction tool are female threads that are sized and shaped to couple to a male thread of the stem component of a femoral trial system and a male thread of the stem component of a tibial trial system, and the second plurality of threads of the first extraction tool are male threads that are sized and shaped to couple to a female thread of the stem stabilizer.

3. The surgical instrument extraction system of claim 2, wherein:

the stem component of the femoral trial system couples to the intermediate trial component of the femoral trial system, and the stem component of the tibial trial system couples to the intermediate trial component of the tibial trial system.

4. The surgical instrument extraction system of claim 3, wherein:

the stem component of the femoral trial system is a femoral stem trial, and the stem component of the tibial trial system is a tibial stem trial.

5. The surgical instrument extraction system of claim 1, wherein:

the first plurality of threads of the second extraction tool are male threads that are sized and shaped to couple to a female thread of the intermediate trial component of a tibial trial system, and the second plurality of threads of the second extraction tool are male threads that are sized and shaped to couple to a female thread of the intermediate trial component of a femoral trial system.

6. The surgical instrument extraction system of claim 5, wherein the first plurality of threads of the second extraction tool has a first thread diameter and the second plurality of threads of the second extraction tool has a second thread diameter, the second threads diameter being greater than the first thread diameter.

7. The surgical instrument extraction system of claim 6, wherein the first end of the second extraction tool is a tapered end that tapers from the second body to the first diameter.

8. The surgical instrument extraction system of claim 7, wherein the tapered end is sized and shaped to be received in a bore extending through a side of the stem stabilizer to remove the stem stabilizer from the femoral intramedullary adaptor.

9. The surgical instrument extraction system of claim 5, wherein:

the intermediate trial component of a tibial trial system couples to a surface tibial trial of the tibial trial system, and the intermediate trial component of the femoral trial system couples to a surface femoral trial of the femoral trial system.

10. The surgical instrument extraction system of claim 9, wherein:

the intermediate trial component of a tibial trial system is at least one of a fixed bearing adaptor trial, a fixed bearing stem adaptor trial, a rotating platform stem adaptor trial, or a tibial offset adaptor trial, and the intermediate trial component of the femoral trial system is at least one of a boss adaptor trial or a femoral offset adaptor trial.

\* \* \* \* \*